(12) United States Patent
Bernard De Man et al.

(10) Patent No.: US 7,885,375 B2
(45) Date of Patent: Feb. 8, 2011

(54) METHOD AND SYSTEM FOR X-RAY IMAGING

(75) Inventors: Bruno Kristiaan Bernard De Man, Clifton Park, NY (US); Daniel David Harrison, Delanson, NY (US); Maria Iatrou, Clifton Park, NY (US); Brian Patrick Smyth, San Francisco, CA (US); Zhye Yin, Schenectady, NY (US); Samit Kumar Basu, Fremont, CA (US); Souma Sengupta, Foster City, CA (US); Peter Claudius Sanza, Wilmington, NC (US)

(73) Assignee: General Electric Company, Niskayuna, NY (US)

( * ) Notice: Subject to any disclaimer, the term of this patent is extended or adjusted under 35 U.S.C. 154(b) by 116 days.

(21) Appl. No.: 12/254,732

(22) Filed: Oct. 20, 2008

(65) Prior Publication Data

US 2009/0161816 A1    Jun. 25, 2009

Related U.S. Application Data

(63) Continuation-in-part of application No. 11/970,403, filed on Jan. 7, 2008, now Pat. No. 7,639,775, which is a continuation of application No. 10/789,539, filed on Feb. 27, 2004, now Pat. No. 7,333,587.

(51) Int. Cl.
*G01N 23/00* (2006.01)
(52) U.S. Cl. .......................................... 378/9; 378/122
(58) Field of Classification Search .................. 378/9, 378/10, 12, 122
See application file for complete search history.

(56) References Cited

U.S. PATENT DOCUMENTS

| | | | |
|---|---|---|---|
| 4,129,783 A | 12/1978 | Houston | |
| 4,149,082 A | 4/1979 | Haendle et al. | |
| 4,592,079 A | 5/1986 | Sohval et al. | |
| 5,570,403 A | 10/1996 | Yamazaki et al. | |
| 6,041,097 A | 3/2000 | Roos et al. | |
| 6,385,280 B1 | 5/2002 | Bittl | |
| 7,187,748 B2 | 3/2007 | Hoffman | |
| 7,277,523 B2 | 10/2007 | Mattson | |
| 7,280,631 B2 | 10/2007 | De Man et al. | |
| 7,317,783 B2 | 1/2008 | Dolgonos | |
| 2003/0048868 A1 | 3/2003 | Bailey et al. | |
| 2004/0258196 A1 | 12/2004 | Lounsberry | |
| 2005/0232389 A1* | 10/2005 | Klingenbeck-Regn | 378/9 |
| 2007/0092058 A1 | 4/2007 | Mattson | |
| 2007/0133747 A1* | 6/2007 | Manak et al. | 378/62 |
| 2007/0248213 A1 | 10/2007 | Dolgonos | |
| 2010/0061512 A1* | 3/2010 | Edic et al. | 378/71 |

FOREIGN PATENT DOCUMENTS

JP    2004006349    1/2004

* cited by examiner

*Primary Examiner*—Hoon Song
(74) *Attorney, Agent, or Firm*—Jason K. Klindtworth

(57) ABSTRACT

A technique is provided for imaging a field of view using an X-ray source comprising two or more emission points. The two or more emission points may be independently operated. Independent operation of the two or more emission points in performed in accordance with a list of commands that specifies the operation of the emission points. The list of commands, in one embodiment, is stored in a sequence buffer. In other embodiments, the list of commands is generated for a given usage, without being stored in a sequence buffer.

24 Claims, 9 Drawing Sheets

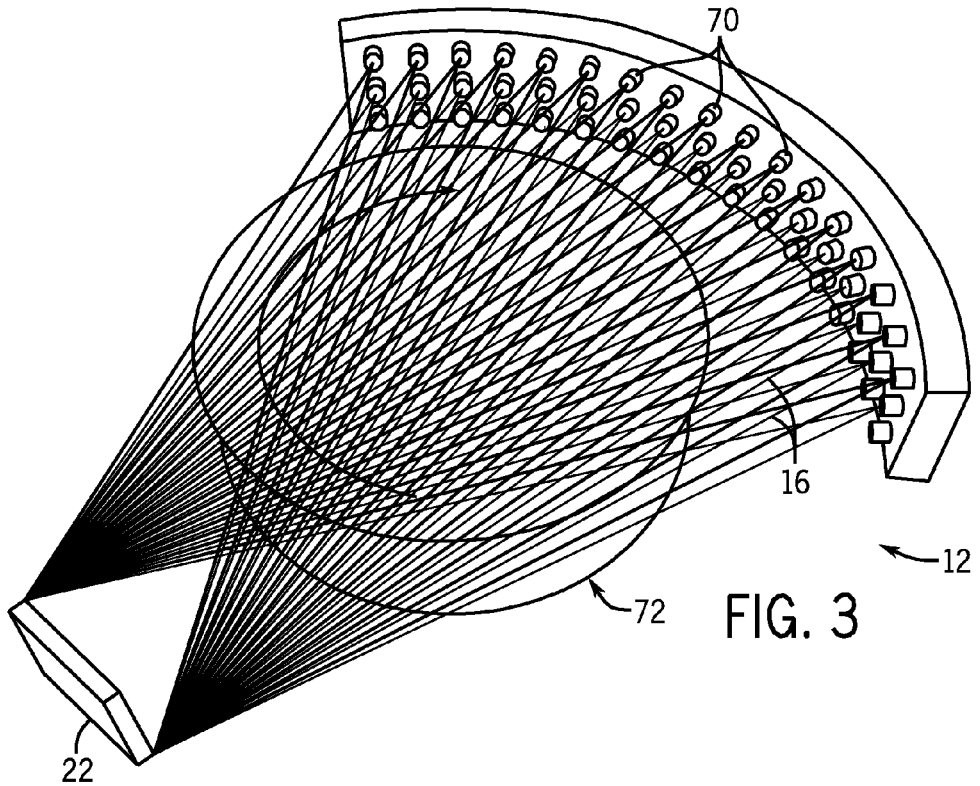
FIG. 3
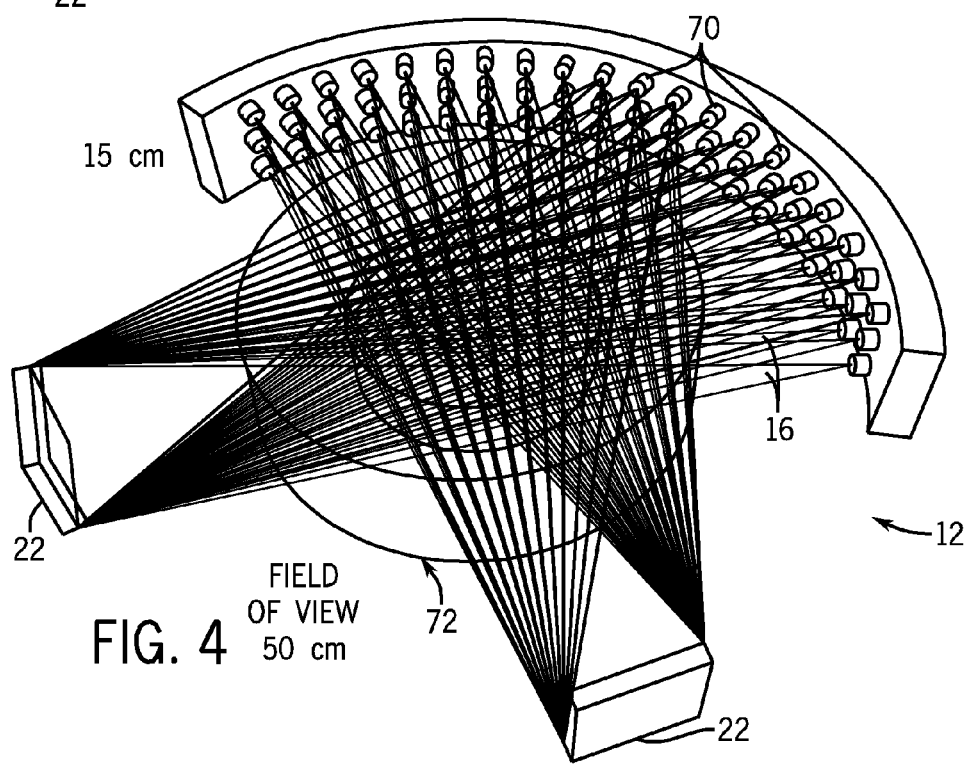
FIG. 4 FIELD OF VIEW 50 cm

METHOD AND SYSTEM FOR X-RAY IMAGING

CROSS REFERENCE TO RELATED APPLICATIONS

This application is a Continuation-in-Part of U.S. patent application Ser. No. 11/970,403, entitled "Method and System for Imaging Using Multiple Offset X-Ray Emission Points", filed Jan. 7, 2008, which is a continuation of U.S. patent application Ser. No. 10/789,539, entitled "Method and System for Imaging Using Multiple Offset X-Ray Emission Points", filed Feb. 27, 2004, which are both herein incorporated by reference in their entirety for all purposes.

STATEMENT REGARDING FEDERALLY SPONSORED RESEARCH & DEVELOPMENT

This invention was made with Government support under contract number R01 EB006837 awarded by the National Institute of Health. The Government has certain rights in the invention.

BACKGROUND OF THE INVENTION

The present disclosure relates generally to the field of non-invasive imaging and more specifically to the field of computed tomography (CT) imaging. In particular, the present disclosure relates to scanner configurations and command sequences useful in CT imaging.

CT scanners operate by projecting fan-shaped or cone-shaped X-ray beams from an X-ray source. The X-ray source emits X-rays at numerous view angle positions about an object being imaged, such as a patient, which attenuates the X-ray beams as they pass through. The attenuated beams are detected by a set of detector elements, which produce signals representing the intensity of the incident X-ray beams. The signals are processed to produce data representing the line integrals of the attenuation coefficients of the object along the X-ray paths. These signals are typically called "projection data" or just "projections". By using reconstruction techniques, such as filtered backprojection, useful images may be formulated from the projections. The images may in turn be associated to form a volume rendering of a region of interest. In a medical context, pathologies or other structures of interest may then be located or identified from the reconstructed images or rendered volume. In other contexts, items or structures within baggage or packages or defects in manufactured goods may be ascertained.

It is generally desirable to develop CT scanners with high spatial and temporal resolution, good image quality, and good coverage along the z-axis, i.e., the longitudinal axis of the CT scanner. To meet some or all of these objectives, it may be desirable to increase the coverage provided by the detector, thereby allowing greater scan coverage in one or more dimensions. For example, longitudinal axis coverage of the detector may be improved by increasing the number of rows of detector elements in the detector.

This approach has lead to the development of CT systems with larger detectors. Larger detectors, however, may be undesirable for a variety of reasons. For instance, as one might expect, larger detectors and associated acquisition electronics are both more costly and more difficult to produce. In addition, the mechanical subsystem responsible for supporting and/or rotating a larger detector may also need to be larger and more complex and/or may be subject to greater mechanical stress. Furthermore, large detectors are associated with increased cone angles, i.e., the angle subtended by the outer detector rows to the source focal spot. The increased cone angle subtended by the detector longitudinal boundaries is in turn associated with increased cone-beam artifacts in the reconstructed images. When the cone angle increases beyond a certain limit, the degradation of the image quality may become severe for axial, or step and shoot scanning. For this reason, it may be difficult to increase the scan coverage by simply increasing the longitudinal size of the detector. A technique for achieving high spatial and temporal resolution, good image quality, and good coverage using a standard or smaller detector may therefore be desirable.

BRIEF DESCRIPTION OF THE INVENTION

The present technique provides a novel method and apparatus for providing two or more discrete X-ray emission points, i.e., focal spots, which are laterally offset, i.e., have different xy-coordinates and/or longitudinally offset, i.e., have different z-coordinates. For example, the sources may be offset in an azimuthal direction such that, after rotation, each source provides a particular subset of the projection lines needed to reconstruct the imaged object within the field of view. The sources may be alternately activated, though not necessarily at equal intervals, i.e., some of the sources may be activated more frequently or for greater duration than others. One or more detectors may be employed in conjunction with the two of more sources. In one embodiment, a detector may have a relatively small in-plane extent and may be a flat-panel detector in some implementations.

In certain embodiments, the operation of the individual focal spots, in terms of activation timing, energy, duration, focal spot size, and so forth, may be specified by a list of commands or instructions. Likewise the activation and operation of one or more detectors or other aspects of the CT system may be specified by a list of commands or instructions. Such a list of commands for focal spot operation, detector operation, or control of other aspects of the CT system may be referred to as a command sequence. Such a command sequence may be stored in a sequence buffer of the CT system or may be transmitted to the CT system concurrent with the operation of the CT system. There may be a single command associated with each single X-ray pulse and/or with each single detector frame.

In accordance with one embodiment, a CT imaging system is provided. The CT imaging system includes a plurality of discrete X-ray emission focal spots and one or more detectors configured to detect X-rays emitted by the plurality of X-ray emission focal spots. The CT imaging system also includes an X-ray controller configured to independently operate the plurality of discrete X-ray emission focal spots and a data acquisition system configured to readout signals from the one or more detectors. The CT imaging system also includes a sequence buffer configured to store a list of commands controlling the operation of the X-ray controller.

In accordance with a further embodiment, a sequence buffer is provided. The sequence buffer comprises a data storage structure. A command sequence is physically encoded on the data storage structure. The command sequence comprises instructions for independently operating a plurality of X-ray emission focal spots of a distributed X-ray source.

In accordance with an additional embodiment, a method is provided. The method includes the act of processing a list of commands related to the operation of an imaging system. A plurality of X-ray focal spots of a distributed X-ray source are individually operated in accordance with the list of commands.

In accordance with another embodiment, a method is provided. The method includes the act of providing a distributed X-ray source comprising a plurality of discrete and separately operable X-ray emission focal spots. One or more detectors configured to generate signals in response to X-rays emitted by the distributed X-ray source are also provided. A sequence buffer capable of storing a list of commands for operating the plurality of X-ray emission focal spots is also provided. An X-ray controller is electrically connected to the distributed X-ray source and the sequence buffer. The X-ray controller is capable of independently operating the plurality X-ray emission focal spots in accordance with the list of commands. A data acquisition system is electrically connected to the one or more detectors. The data acquisition system is capable of reading out the signals generated by the one or more detectors

BRIEF DESCRIPTION OF THE DRAWINGS

The foregoing and other advantages and features of the invention will become apparent upon reading the following detailed description and upon reference to the drawings in which:

FIG. 3 is an illustration of one possible distributed X-ray source and detector configuration in accordance with a present embodiment;

FIG. 4. is an illustration of another possible distributed X-ray source and detector configuration in accordance with a further present embodiment;

DETAILED DESCRIPTION OF SPECIFIC EMBODIMENTS

Figure 1:
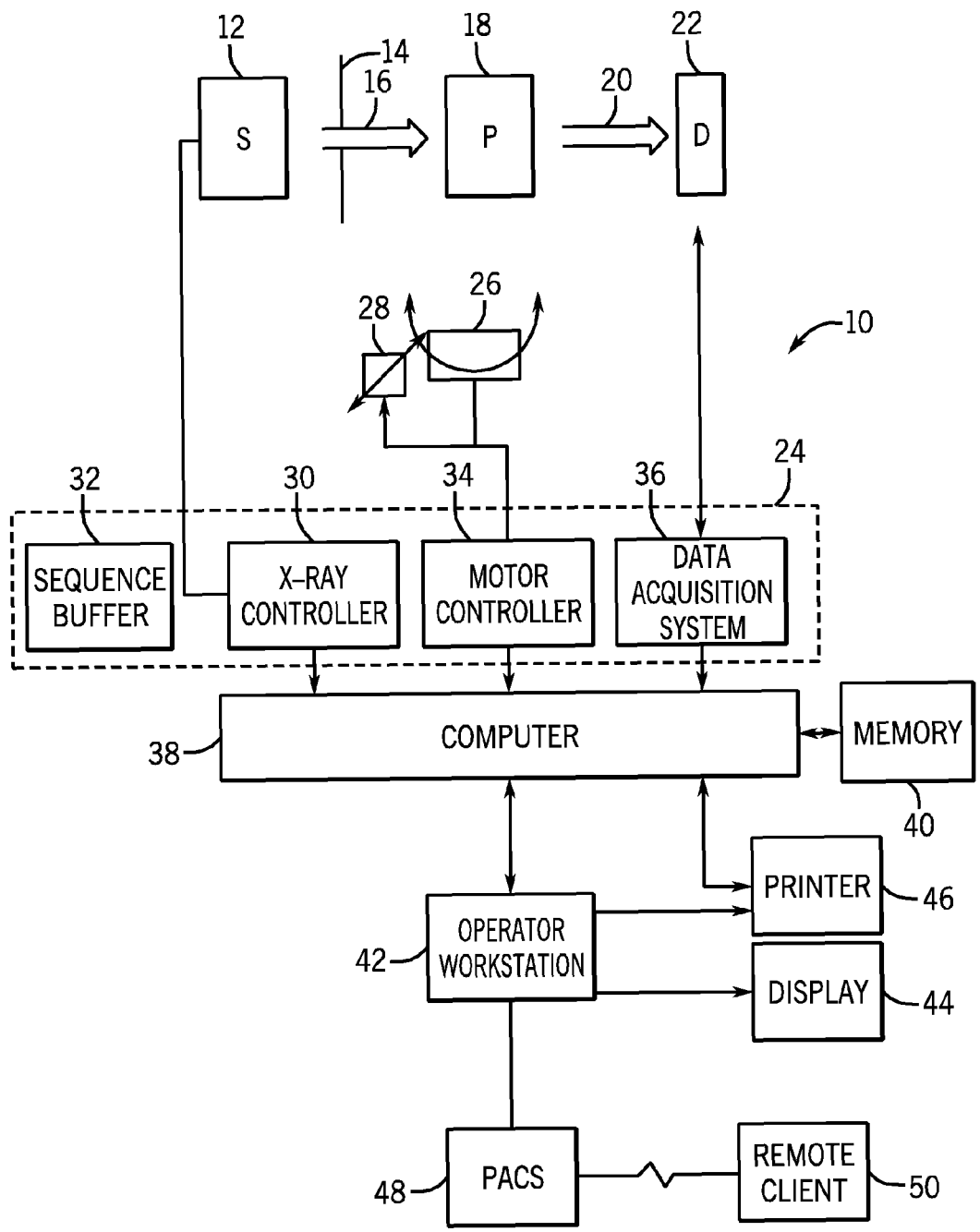
FIG. 1 is a diagrammatical view of an exemplary imaging system in the form of a CT imaging system for use in producing processed images, in accordance with a present embodiment.

FIG. 1 illustrates diagrammatically an imaging system 10 for acquiring and processing image data. In the illustrated embodiment, system 10 is a computed tomography (CT) system designed to acquire X-ray projection data, to reconstruct the projection data into an image, and to process the image data for display and analysis in accordance with the present technique. Though the imaging system 10 is discussed in the context of medical imaging, the techniques and configurations discussed herein are applicable in other non-invasive CT imaging contexts, such as baggage or package screening and/or manufacturing quality control.

In the embodiment illustrated in FIG. 1, CT imaging system 10 includes a source 12 of X-ray radiation. As discussed in detail herein, the source 12 of X-ray radiation may consist of two or more discrete, i.e., separated, emission points or foci for X-ray emission. For example, a conventional X-ray tube may be equated with a single emission point. Alternatively, an X-ray source such as a solid-state X-ray source having field emitters, or a thermionic X-ray source may include multiple emission points. Such solid-state or thermionic X-ray sources may be configured such that the respective emission points form a stationary or rotating array or a stationary ring.

Though the present description may discuss the rotation of an X-ray source 12, as may occur in conventional third-generation CT systems, such discussion of a rotating an X-ray source 12 also encompasses functional equivalents. For example, for a solid-state X-ray source 12 configured as a ring, the source 12 and respective emission points may not physically rotate. Instead, emission points along the ring may be activated in a sequential or non-sequential manner effectively equivalent to rotating an X-ray source 12 about the imaging volume. Therefore, where an X-ray source 12 or emission point is described as rotating, it is to be understood that such a rotation may result from the physical rotation of the source 12 or elements of source 12 or from such a functional equivalent.

As noted above, in certain embodiments, the X-ray source 12 may be a distributed X-ray source that allows X-rays to be generated over a wide range of focal spot (i.e., emission point) positions. For example, in a distributed X-ray source embodiment, the respective emission points may be separated by tens of centimeters, such as by 10 cm, 15 cm, 20 cm, 25 cm, 30 cm, and so forth. Such a distributed X-ray source may be useful for generating X-rays that traverse substantially different portions of the patient or object being imaged and/or for generating X-rays that traverse the patient or object being imaged at substantially different azimuthal angles.

Examples of such distributed X-ray sources include electron-beam CT scanners which generate X-rays by sweeping an electron-beam over one or more target rings that surround the scanner field-of-view. Such an arrangement can generate X-rays from different azimuthal angles in a rapid scan sequence. Other scanning-beam X-ray sources may also be understood to be distributed X-ray sources. In addition, in certain embodiments, distributed X-ray sources may be stationary in nature, employing no mechanical motion to generate X-rays at different views about the patient or object being imaged. In such stationary embodiments, the distributed source can be based on one or more sweeping electron beams or on a plurality of discrete electron emitters, or a combination of the two techniques. In addition, in certain embodiments, the distributed source architecture may be rotated. For example, in one such embodiment, the distributed X-ray source may be based on a 2D-array of discrete electron emitters.

In some embodiments, the X-ray source 12 may be positioned proximate to a collimator 14. The collimator 14 may consist of a collimating region, such as lead or tungsten shutters, for each emission point of the source 12. The collimator 14 typically defines the size and shape of the one or more streams of radiation 16 that pass into a region in which a subject, such as a human patient 18, is positioned. A stream of radiation 16 may be generally cone-shaped, depending on the configuration of the detector array, discussed below, as well as the desired method of data acquisition. An attenuated portion of the radiation 20 passes through the subject, which provides the attenuation, and impacts a detector array, represented generally at reference numeral 22.

The detector 22 is generally formed by a plurality of detector elements, which detect the X-rays that pass through and adjacent to a subject of interest. The detector 22 may include multiple rows of detector elements. When such multi-row detectors are employed, the stream of radiation 16 will have a non-zero cone-angle associated with it for detector rows not in-plane with the active emission point. The following examples may make abstraction of this z-extent to simplify presentation, i.e., by limiting discussion to the detector elements in-plane with the active emission point. However, the following geometrical discussion and examples are equally applicable to multi-row detectors.

Each detector element, when impacted by an X-ray, produces an electrical signal that represents the intensity of the X-ray beam at the position of the element during the time the beam strikes the detector. Typically, signals are acquired at a variety of view angle positions around the subject of interest so that a plurality of radiographic views may be collected. These signals are acquired and processed to reconstruct an image of the features within the subject, as described below.

The X-ray source 12 is controlled by a system controller 24, which furnishes power, focal spot location, control signals and so forth for CT examination sequences. Moreover, the detector 22 is coupled to the system controller 24, which commands acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system 10 to execute examination protocols and to process acquired data. In the present context, system controller 24 also includes signal processing circuitry, typically based upon a general purpose or application-specific digital computer, and associated memory circuitry. The associated memory circuitry may store programs and routines (such as programs, routines, and/or algorithms for implementing the presently disclosed subject matter), configuration parameters, image data, and so forth.

In the embodiment illustrated in FIG. 1, system controller 24 may control the movement of a rotational subsystem 26 and linear positioning subsystem 28 via a motor controller 34. In an imaging system 10 in which the source 12 and/or the detector 22 may be rotated, the rotational subsystem 26 may rotate the X-ray source 12, the collimator 14, and/or the detector 22 through one or multiple turns around the patient 18. It should be noted that the rotational subsystem 26 might include a gantry. The linear positioning subsystem 28 enables the patient 18, or more specifically a patient table, to be displaced linearly. Thus, the patient table may be linearly moved within the gantry to generate images of particular areas of the patient 18.

The source 12 of radiation may be controlled by an X-ray controller 30 disposed within the system controller 24. The X-ray controller 30 may be configured to provide power and timing signals to the X-ray source 12. In addition, the X-ray controller may be configured to provide focal spot location, i.e., emission point activation, if the X-ray source 12 is a distributed source, such as a solid-state or thermionic X-ray source configured as an array or ring. For example, the X-ray controller 30 may be implemented as high-voltage switching circuitry to switch on and off the individual focal spots, i.e., emission points, in a distributed X-ray source. Such circuitry may include or communicate with a logical controller to control various high-voltage stages.

In one embodiment, the X-ray controller 30 may include or be in communication with a sequence buffer 32 storing various commands or instructions, such as command sequences, for operating different focal spots of the X-ray source 12, as discussed herein. In particular, different X-ray focal spot command sequences may be used to vary the image quality, noise, scatter, X-ray source thermals, patient dose, or other parameters associated with operation of the imaging system 10. For example, a command sequence may be a list of commands where each command contains the indices of the focal spots to be activated, as well as the mA, the kVp, focal spot size, and/or the dwell time (pulse duration) for each focal spot activation. The sequence buffer 32 may also store hard coded or programmable "dead-times" between focal spot activations to help reduce crosstalk. In addition a command sequence stored in the sequence buffer 32 may include detector modes (such as photon counting versus energy integrating mode, high flux versus low flux mode, and so forth) that may be utilized by the X-ray controller 30 and/or the data acquisition system 36 during operation. In practice, the sequence buffer 32 may be implemented as a memory device or other storage structure suitable for storing computer implemented instructions. For example, the sequence buffer 32 may be embodied as a solid state memory device, (such as a memory chip used as a ROM or a RAM in a processor based system or as a solid state hard drive), as an optical storage device (such as an optical disk), as a magnetic storage device (such as a conventional hard drive), or as any other suitable data storage structure suitable for storing a script of instructions for operation of the individual focal spots of a distributed X-ray source and/or for operation of one or more detectors 22 of the imaging system 10.

The size of the sequence buffer 32 may be based on the length and number of the instructions stored in the sequence buffer 32. In one embodiment, each line of instructions may include a 2 byte field for the sample period number (e.g., sample period, 1, 5, 15, and so forth), a 1 byte field for an operation code, i.e., and instruction (e.g., a code of "7" might indicate an instruction to trigger focal spot 7), three 1 byte fields for modifiers or variables that determine, modify, or complement the operation code or some other aspect of the line of instruction (e.g., codes of "27", "30" and "45" might indicate that the activated source spot is to be activated at 27 mA for 30 μs, 45 μs after a trigger is received. This may be added to 6 bytes in a typical sub-view. In one such embodiment, therefore, the sequence buffer size, assuming a sampling rate of 7 kHz, is 42 kB+a kB per second of scanning. In other implementations, the sequence buffer size may be about 50 kB to about 60 kB per second.

In some embodiments, the sequence buffer 32 may not be present in the system controller or may not be utilized. For example, in certain embodiments, a processor and suitable memory (which may or may not be the sequence buffer 32 or the memory 40) in communication with the processor may be used to generate a command sequence as described above for immediate use, i.e., the command sequence may be generated ad hoc or "on-the-fly", without relying on pre-stored or pre-generated sequences. Such a processor and suitable memory may be associated with the system controller 24, computer 38, or other suitable processor-based systems in communication with or forming the CT system 10. Thus, in such embodiments, a sequence buffer 32 or other memory structure, e.g., memory 40, may be present but may be used not as a storage buffer but as a staging area for generation and immediate use of the generated command sequence.

In embodiments where the sequence buffer 32 is not present or is not provided as part of the system controller 24, commands may instead be transmitted in real time to the system controller 24 and the data payload on the link may be lower than the raw content of the sequence buffer. In an embodiment having a distributed X-ray source having 50 focal spots and 20 possible grid levels (i.e., mA levels), given that a sample period number would not have to be transmitted, 3 bytes per typical sample period would be sufficient, 6 bytes if two focal spots are activated simultaneously. Assuming a 7 kHz sampling rate, a baud rate greater than or equal to 500 kbaud would be sufficient.

Figure 2:
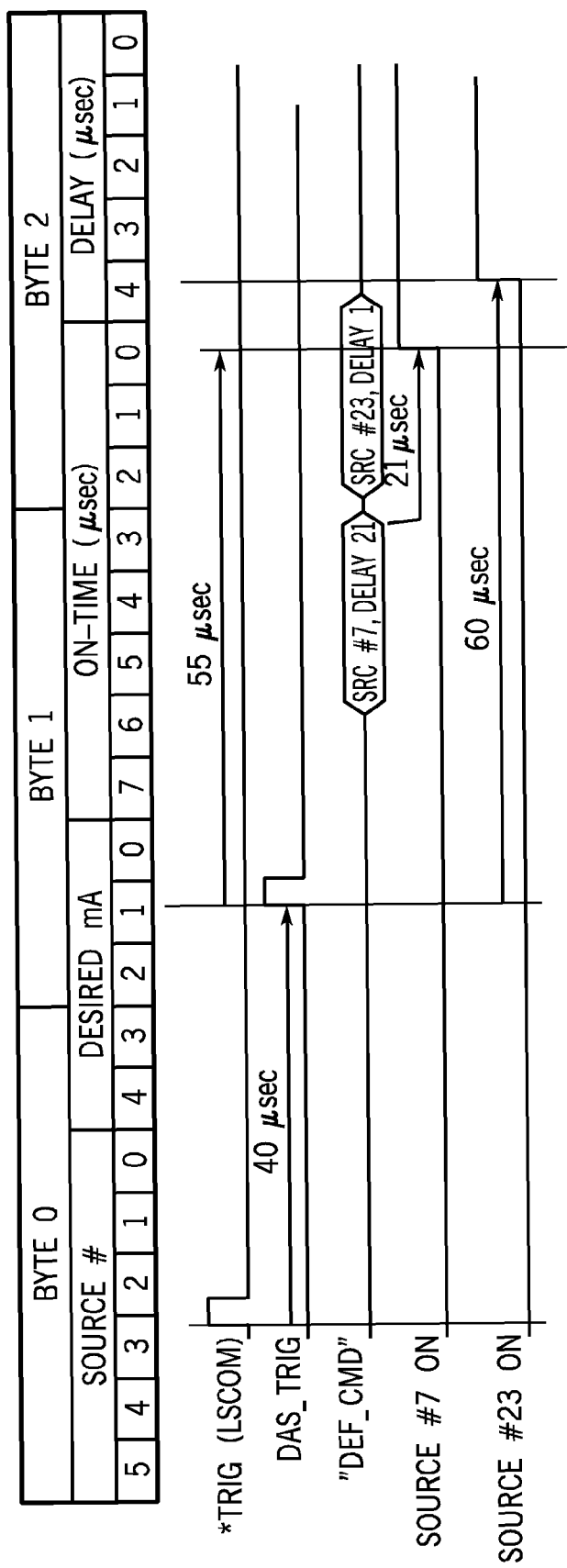
FIG. 2 is timing diagram of an exemplary command sequence in accordance with a present embodiment.

In certain embodiments, the delay in μs between focal spot activations can be encoded using only 5 bits (i.e., 0-4). In one such embodiment, two focal spots may be activated in the same sample period but at different times after a trigger. For example, a first focal spot may be instructed to activate 55 μs after a trigger while a second focal spot may be instructed to activate 60 μs after the trigger. In such an implementation, 5 bits may not be enough to transmit these delays, however the logic executing the instructions in the sequence buffer may instead delay transmission of the command for a suitable time to effectively achieve the desired delay, such as until less than 31 μs remains in the present example. A representation of such a packing scheme provided with a fixed latency of 40 μs is provided in FIG. 2.

The system controller 24 may also comprise a data acquisition system (DAS) 36, such as detector electronics that collect and amplify the respective signals from the cells of the detector 22. In this exemplary embodiment, the detector 22 is coupled to the system controller 24, and more particularly to the data acquisition system 36. The data acquisition system 36 receives data collected by readout electronics of the detector 22. In particular, the data acquisition system 36 typically receives sampled analog signals from the detector 22 and converts the data to digital signals for subsequent processing by a computer 38.

The computer 38 is typically coupled to the system controller 24. The data collected by the data acquisition system 36 may be transmitted to the computer 38 for subsequent processing and reconstruction. For example, the data collected from the detector 22 may undergo pre-processing and calibration at the data acquisition system 36 and/or the computer 38 to condition the data to represent the line integrals of the attenuation coefficients of the scanned objects. The processed data, commonly called projections, may then be reordered, filtered, and backprojected to formulate an image of the scanned area. Once reconstructed, the image produced by the system of FIG. 1 reveals an internal region of interest of the patient 18 which may be used for diagnosis, evaluation, and so forth.

The computer 38 may comprise or communicate with a memory 40 that can store data processed by the computer 38 or data to be processed by the computer 38. It should be understood that any type of computer accessible memory device (e.g., solid state memory devices, hard drives, optical disks, and so forth) capable of storing the desired amount of data and/or code may be utilized by such an exemplary system 10. Moreover, the memory 40 may comprise one or more memory devices, such as solid state, magnetic or optical devices, of similar or different types, which may be local and/or remote to the system 10. The memory 40 may store data, processing parameters, and/or computer programs comprising one or more routines for performing the processes described herein.

The computer 38 may also be adapted to control features enabled by the system controller 24, i.e., scanning operations and data acquisition. Furthermore, the computer 38 may be configured to receive commands and scanning parameters from an operator via an operator workstation 42 which may be equipped with a keyboard and/or other input devices. An operator may thereby control the system 10 via the operator workstation 42. Thus, the operator may observe the reconstructed image and other data relevant to the system from computer 38, initiate imaging, and so forth.

A display 44 coupled to the operator workstation 42 may be utilized to observe the reconstructed image. Additionally, the scanned image may be printed by a printer 46 which may be coupled to the operator workstation 42. The display 44 and printer 46 may also be connected to the computer 38, either directly or via the operator workstation 42. Further, the operator workstation 42 may also be coupled to a picture archiving and communications system (PACS) 48. It should be noted that PACS 48 might be coupled to a remote system 50, radiology department information system (RIS), hospital information system (HIS) or to an internal or external network, so that others at different locations may gain access to the image data.

One or more operator workstations 42 may be linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

The CT imaging system 10 described above may be configured in a variety of ways to improve spatial and temporal resolution, to improve image quality, to reduce patient radiation dose and/or to improve longitudinal coverage. Indeed, various source 12 and detector 22 configurations may be implemented which improve one or more of these parameters. For example, as discussed herein, an X-ray source 12 that employs multiple emission points, i.e., focal spots, may be employed. Activation of the emission points may be coordinated so that only one is active at a time, such as by employing an alternating activation scheme, or to allow simultaneous activations. In this manner, each emission point, when active, may provide a subset of the projection lines required to reconstruct an object within a given field of view. Combination of these subsets, however, allows the reconstruction of the field of view. In addition, in embodiments where only a subset of the projection lines associated with the field of view are acquired at one time, the in-plane extent of the detector 22 may be reduced. Indeed, the in-plane extent of the detector 22 may be reduced to the degree that a flat-panel detector, i.e., a radiographic detector panel, may be employed.

A variety of X-ray source 12 configurations and activation schemes may be practiced in accordance with the present technique. A number of exemplary configurations and schemes are discussed herein. It is to be understood, however, that the included examples do not limit the scope of the present technique. Instead, the present technique may broadly be understood to encompass any X-ray source configuration that allows for multiple, discrete emission points as well as any activation scheme for such emission points.

For example, referring now to FIGS. 3 and 4, examples of different distributed X-ray source 12 configurations are described. In the example illustrated in FIG. 3, a standard array-source inverse-geometry CT architecture is depicted. In this example, an X-ray source 12 is depicted which consists of 20×3 focal spots, i.e., emission points 70, distributed in x (azimuthally) and z (longitudinally) respectively. As will be appreciated, similar geometries may be employed that utilize different numbers of emission points 70, such as 1, 2, 3, 4, 5, . . . , 100 or more emission points in z and 2, 3, 4, . . . , 1,000 or more emission points in x. The depicted architecture includes a detector 22, such as a flat panel detector. In one embodiment, the detector 22 is about 10 cm×10 cm. The emission points 70 emit X-rays 16 through a field of view 72 to impact the detector 22.

In the example depicted in FIG. 4 a cardiac version of an inverse-geometry CT architecture is depicted. In this example, the distributed X-ray source 12 has about 30×3 emission points distributed in x (azimuthally) and z (longitudinally) respectively and two detectors 22. In one embodiment, the detectors 22 are about 10 cm×10 cm each. In other embodiments, more that two detectors 22 may be employed. As will be appreciated, similar geometries may be employed that utilize different numbers of emission points 70, such as 1, 2, 3, 4, 5, . . . , 100 or more emission points in z and 2, 3, 4, . . . , 1,000 or more emission points in x.

Figure 5:
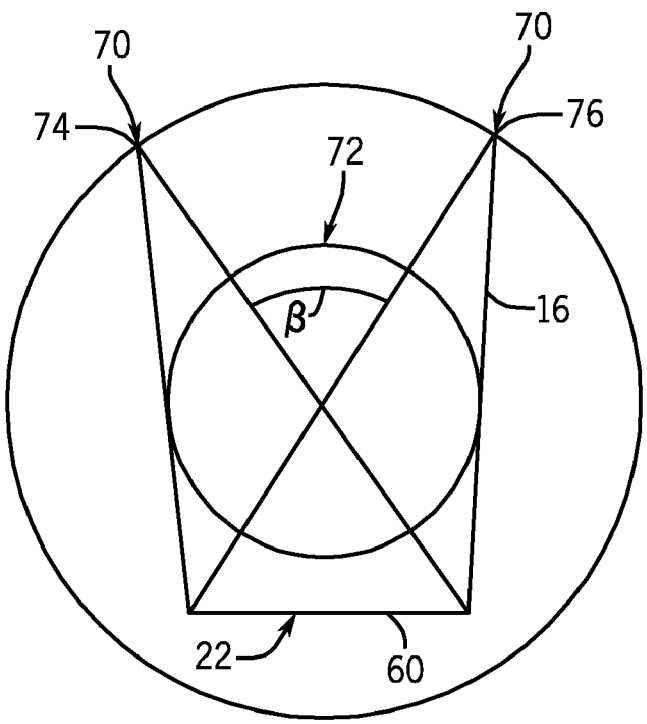
FIG. 5 is an in-plane view of a pair of X-ray emission points in a full field-of-view configuration, in accordance with a present embodiment.

With the foregoing discussion of exemplary distributed X-ray sources in mind, the following simplified examples describe several embodiments of the present technique with respect to emission point configurations in the x direction. For example, as depicted in FIG. 5, a pair of discrete emission points 70 offset in an azimuthal direction are depicted in an xy-plane, as the source 12 of radiation. The emission points 70 may be configured to be the same perpendicular distance from the detector 22, such as flat-panel detector 60, or may be different distances. Each emission point 70 may be an X-ray tube, a focal spot of a distributed X-ray source based on solid-state or thermionic electron emitters, or some other focal point from which X-rays may be emitted when activated. The X-ray source 12, and its respective emission points 70, may be gridded. The emission points 70 may also be offset in z, as discussed herein.

The emission points 70 may be rotated about the desired field of view 72, allowing each emission point 70 to emit streams of radiation 16 from the desired view angles. As the emission points 70 rotate, they may be alternatingly activated such that only one emission point 70 emits X-rays at a given time. Each emission point 70 may be configured to emit a fan-shaped stream of radiation when activated, which circumscribes a portion of the field of view 72, such as half the field of view 72 as depicted in FIG. 5. The stream of radiation 16 passes through the field of view 72, and any attenuating matter within the field of view 72, before striking the detector 22, such as flat-panel detector 60. For each activation of an emission point 70, the data acquisition system 36 (FIG. 1) reads out the signals generated by the detector 22, which may be processed to generate the projection data. As the emission points 70 rotate about the field of view 72 the combined or aggregate acquired projection data describes the entire field of view.

For example, a first emission point 74, when active, may emit X-rays within a fan encompassing a portion of the field of view 72, such as half the field of view 72, as depicted in FIG. 5. Projection data may, therefore, be acquired for this portion by the detector 22, such as flat-panel detector 60, when the first emission point 74 is active. When the first emission point 74 is inactive, the second emission point 76 may be activated, allowing projection data to be acquired for a portion of the field of view 72 encompassed by the fan of X-rays emitted by second emission point 76. The emission points 70 may be rotated about the field of view 72, being alternatingly activated at each desired view angle, until the desired projection data has been acquired to reconstruct the field of view 72.

As will be appreciated by one of ordinary skill in the art, sufficient projection data to reconstruct the field of view 72 may be acquired with less than a full rotation of the emission points 70 about the field of view 72. Indeed, a half rotation plus the angle ($\beta$) between the two emission points 70, i.e., $180°+\beta$, may be sufficient rotation to provide projection data to reconstruct the field of view 72.

Figure 6:
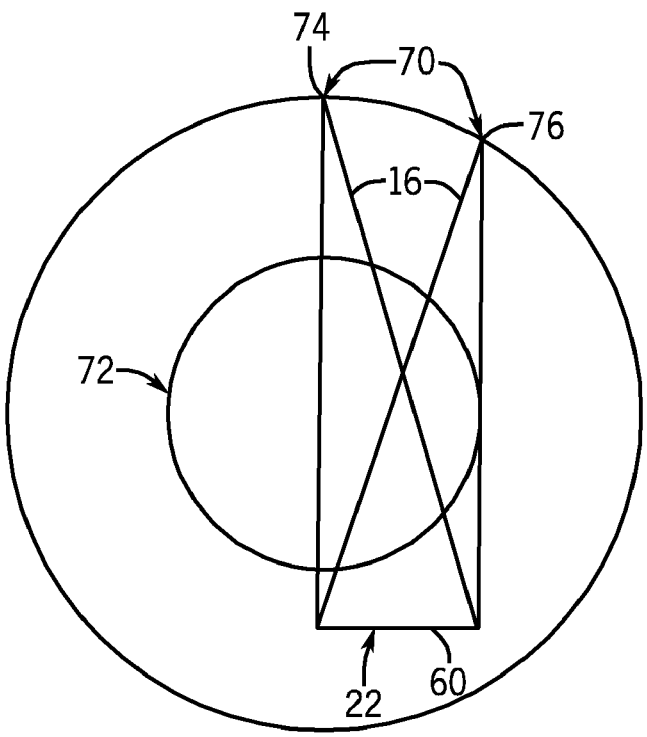
FIG. 6 is an in-plane view of a pair of X-ray emission points in a half field-of-view configuration, in accordance with a present embodiment.

Furthermore, the multiple emission points 70 may be configured so that their combined fans circumscribe only half, or some other portion, of the field of view 72 when active, i.e., a half field of view configuration. For example, referring to FIG. 6, two emission points 70 are depicted which, when active, emit X-rays within a fan encompassing only a portion of half of the field of view 72. The combined fans of the first and second emission points 74, 76, as depicted, circumscribe only half of the field of view 72. Limiting the fan angle, $\alpha$, associated with each emission point 70, allows the in-plane extent of the detector 22, here flat-panel detector 60, to be further reduced since less of the field of view 72 is imaged when an emission point 70 is active. As one of ordinary skill in the art will recognize, sufficient projection data to reconstruct the field of view 72 using a half field of view configuration, as depicted in FIG. 6, may be acquired with a full rotation of the emission points 70 about the field of view 72.

In addition, it should be recognized that the X-ray emitted by the first emission point 74 and the second emission point 76 do not pass through the same regions of the field of view 72. In particular, the X-rays emitted by the first emission point 74 pass through the central region of the field of view 72, where the imaged object or patient is typically centered. Conversely, the X-rays emitted by the second emission point 76 pass through a peripheral region of the field of view 72, which may contain empty space or regions of the imaged patient or object that are of less interest. This relationship remains true as the first and second emission points 74, 76 rotate about the field of view 72, i.e., the first emission point 74 continues to image the central region of the field of view 72 while the second emission point 76 continues to image the periphery of the field of view 72.

Because of this distinction between the first and second emission points 74, 76, the first and second emission points 74, 76 need not be operated equivalently, such as when the periphery of the field of view 72 is of less or no interest. For example, fewer views may be acquired using the second emission point 76 if desired, i.e., the second emission point 76 may be activated less frequently than the first emission point 74. For instance, the second emission point 76 may be activated for every other view, or less, if desired. Similarly, the second emission point 76 may be operated for a reduced duration or duty cycle, or at a lower energy relative to the first emission point 74.

Likewise, the second emission point 76 may be of lower quality, i.e., lower flux, lower spatial resolution and so forth than the first emission point 74, if the peripheral region imaged by the second emission point 76 is less important. In particular, if lower attenuation, lower resolution, and/or higher noise are acceptable for the periphery of the region of interest 72, a lower flux or lower spatial resolution second emission point 76 may be acceptable. Differential activation of the first and second emission points 74, 76 and/or the use of a lower flux second emission point 76 may allow different doses to be applied to the patient 18 at the center and periphery of the region of interest 72. In this manner, the dose received by the patient 18 may be customized based on the circumstances.

Figure 7:
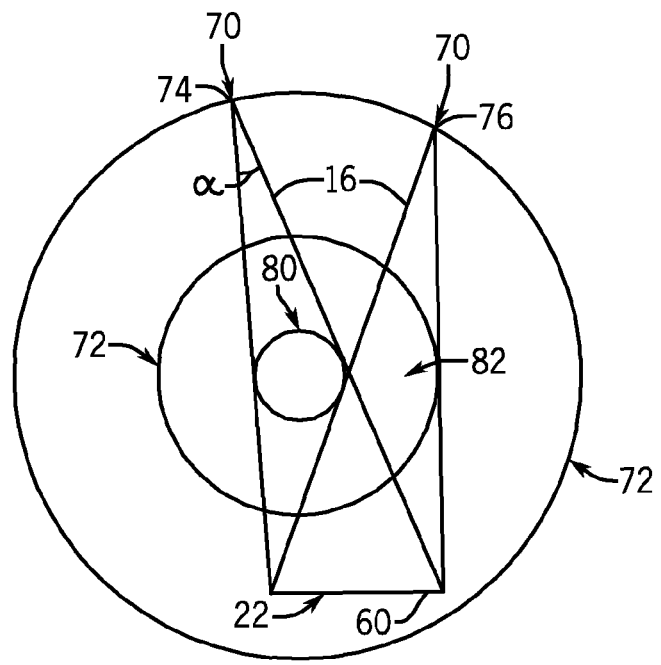
FIG. 7 is an in-plane view of a pair of X-ray emission points in an arbitrary field-of-view configuration, in accordance with a present embodiment.

These concepts may be extended to arbitrary configurations between a half and full field of view configuration or where a distinct central region of interest 80, such as a cardiac field of view, may be present. For example, as depicted in FIG. 7, the first and second emission points 74, 76, may each circumscribe the different portions of the field of view 72, i.e., the central region of interest 80 and the peripheral region 82 respectively. As one of ordinary skill in the art will appreciate, the discussion of the central region of interest 80 and peripheral region 82 with regard to FIG. 7 is analogous to and expands upon the related discussion with regard to FIG. 6.

In particular, referring to FIG. 7, the first emission point 74, when active, may emit X-rays within a fan encompassing the central region of interest 80 within the field of view 72. In this manner, the first emission point 74 may generate the projection lines associated with the central region of interest 80. The second emission point 76, when active, may emit X-rays within a fan encompassing a radial or peripheral portion 82 of the region of interest 72 outside the central region of interest 80. For example, one edge of the fan of X-rays emitted by the second emission point 76 may be tangential to the central region of interest 80 and the other edge may be tangential to the edge of the field of view 72. In this manner, the second emission point 76 may generate projection lines for a complementary portion of the field of view 72 not contained within the central region of interest 80.

As with the preceding examples, because the entire field of view 72 is not covered by a single emission point 70 and detector 22, the in-plane size of the detector 22 may be smaller than if a single emission point 70 were employed. For example, the detector 22 may have a relatively small in-plane extent and, indeed, may be substantially flat, such as flat panel detector 60. For example, for a radius of the central region of interest 80 of 15 cm and a radius of the field of view 72 of 50 cm, the detector 22 may be 30 percent or less of the size of a respective detector associated with the same field of view and a single emission point 70.

Half-scan data acquisition may be used to acquire data for reconstructing the central region of interest 80, i.e., $180°+\alpha$ degrees of rotation. Further, because the fan angle, $\alpha$, is less than when a single emission point 70 is employed, the half-scan may be performed more rapidly, thereby providing improved temporal resolution for imaging dynamic organs such as the heart. For example, $\alpha$ may equal 15° instead of 50° when a second emission point 76 is employed such that the half-scan data acquisition may encompass 195° of rotation of the first emission point 74 instead of 2300 degrees of rotation. However, a full rotation, i.e., 360°, of the first and second emission points 74, 76 may be needed to acquire data for reconstructing the full field of view 72, i.e., to fully reconstruct the peripheral region 82.

As noted above with regard to the half field of view configuration of FIG. 6, fewer views using the second emission point 76 may be acquired if desired, such as when the peripheral views supplied by the second emission point 76 are less important. Similarly, the second emission point 76 may be activated less frequently than the first emission point 74 or for a reduced duration, as discussed in the preceding example. Likewise, as previously discussed, the second emission point 76 may be of lower quality, i.e., lower flux, and so forth than the first emission point 74, if the peripheral region 82 imaged by the second emission point 76 is less important.

Differential activation of the first and second emission points 74, 76 and/or the use of a lower flux second emission point 76 may allow different doses to be applied to the patient 18 inside and outside of the central region of interest 80. Indeed, in some instances, such as where the object or organ to be imaged is within the central region of interest 80, it may be possible to leave the second emission point 76 inactive during image data acquisition. In such an implementation, the data acquired corresponding to the peripheral region 82 will be incomplete, but may still be reconstructed using special reconstruction techniques if desired, such as if some portion of the imaged object lies within the peripheral region 82. In this manner, the dose received by the patient 18 may be customized based on the circumstances.

Though the preceding examples discuss implementations including two emission points 70, the technique is extendable to three or more emission points 70. For example, three or more X-ray tubes may be employed or a solid-state or thermionic X-ray source 12 may be employed which includes three or more addressable emission points 70 configured in an array or ring. Other X-ray sources 12, which include discrete and addressable emission points 70, may also be suitable for use with the present techniques.

Figure 8:
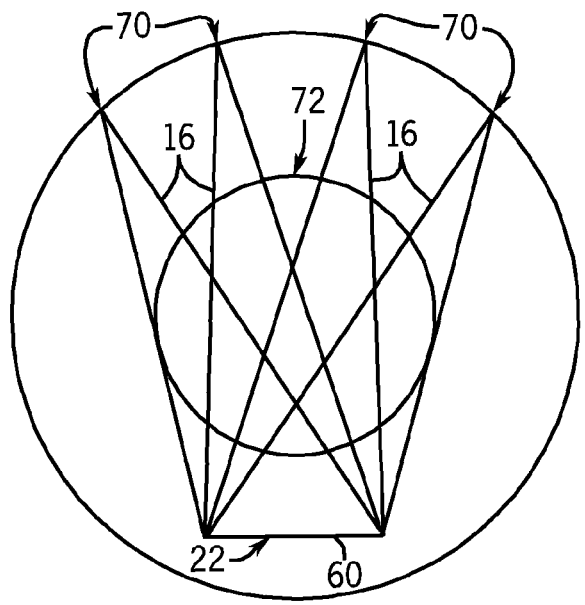
FIG. 8 is an in-plane view of four X-ray emission points in a full field-of-view configuration, in accordance with a present embodiment.

For example, FIG. 8 depicts four emission points 70 in a full field-of-view configuration, analogous to that depicted in FIG. 5. The emission points 70 may be configured to be the same perpendicular distance from the flat-panel detector 60 or may be different distances. As discussed with regard to FIG. 5, the emission points 70 may be rotated about the desired field of view 72 such that each emission point 70 may emit a stream of radiation 16 from the desired view angles.

As the emission points 70 rotate, they may be alternatingly activated such that only one emission point 70 emits X-rays at a given time. Each emission point 70 may be configured to emit a fan-shaped stream of radiation when activated, which circumscribes a portion of the field of view 72. The stream of radiation 16 passes through the field of view 72, and any attenuating matter within the field of view 72, before striking the flat-panel detector 60. For each activation of an emission point 70, the data acquisition system 36 (FIG. 1) reads out the signals generated by the detector 22, which may be processed to generate the projection data. As the emission points 70 rotate about the field of view 72 the combined or aggregate acquired projection data describes the entire field of view. As discussed above, in such a full field-of-view configuration, sufficient projection to reconstruct the field of view 72 may be acquired with a half-scan acquisition, i.e., 180°+some additional angle depending on the geometry.

Similarly, a half field of view configuration may be implemented using more than two emission points 70. For example, referring to FIG. 9, four emission points 70 are depicted whose fan-shaped streams of radiation 16 generally circumscribe half, or some other portion, of the field of view 72. Each emission point 70 may be alternatingly activated, as described above, such that only one emission point 70 is active at a time. Due to the limited fan angle, α, associated with each emission point 70, the detector 22 may have a reduced in-plane extent. In such a half field of view configuration, sufficient projection data to reconstruct the field of view 72 may be acquired with a full rotation of the emission points 70 about the field of view 72.

Figure 9:
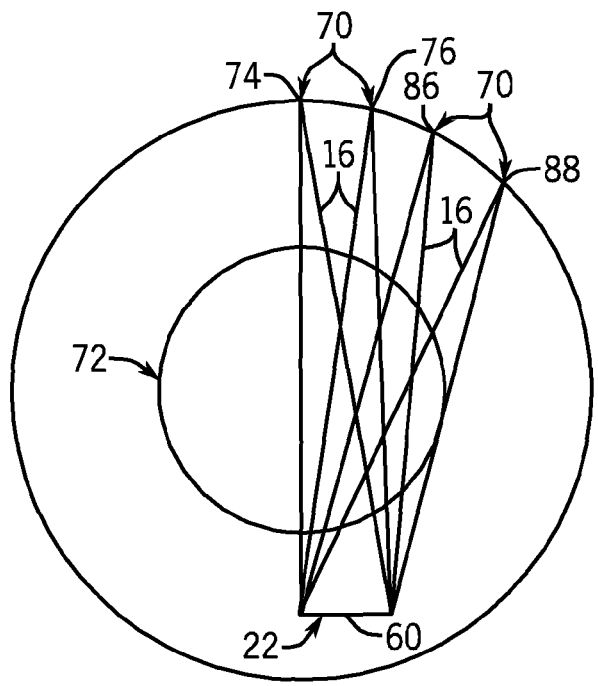
FIG. 9 is an in-plane view of four X-ray emission points in a half field-of-view configuration, in accordance with a present embodiment.

Furthermore, as noted above, the emission points circumscribe different radial regions of the field of view 72. For example, the first emission point 74 defines a central region while the second emission point 76 circumscribes the next outward radial region. Similarly, the third emission point 86 circumscribes the next radial region and the fourth emission point 88 circumscribes the peripheral or outer radial region. Because the emission points 70 circumscribe different radial regions of the field of view 72, different emission points 70 may remain inactive during an imaging sequence if the radial region they circumscribe is of no or little interest. For example, the fourth emission point 88 may remain inactive if the peripheral region of the field of view 72 contains empty space or is otherwise of no interest. As with the previous discussion of a half field of view configuration, sufficient projection data to reconstruct the field of view 72 using a half field of view configuration, as depicted in FIG. 9, may be acquired with a full rotation of the emission points 70 about the field of view 72.

Similarly, and as discussed with regard to FIGS. 6 and 7, the first, second, third, and fourth emission points 74, 76, 86, 88 need not be operated equivalently to the extent that the different radial regions they circumscribe are of different interest or importance. For example, each emission point 70 may be active for different numbers of views. For example, the first and second emission points 74, 76 may be active for every view, the third emission point 86 may be active for every other view, and the fourth emission point 88 may not be active for any view. Such an implementation might allow images to be constructed with good quality toward the center of the field of view, less quality outside of the center, and with no image of the peripheral region of the field of view 72 being generated. Similarly, different emission points, such as the fourth emission point 88, may be operated for a reduced duration or at a lower energy relative to the first emission point 74. Likewise, emission points 70 may vary in quality, i.e., flux, based on the radial region they circumscribe. For example, in an X-ray tube implementation, the third and/or fourth emission points 86, 88 may be low quality, i.e., low flux, X-ray tubes.

Therefore, as the number of X-ray emission points 70 increases, the ability to adapt the X-ray dose to the patient 18 or imaged object may also increase. In particular, possible number of radial regions increases as the number of emission points 70 increases. As the number of radial regions increases, the opportunities to employ differential operation, such as activations and/or durations, or different hardware configurations, such as low-flux X-ray tubes, also increases. In this manner, the dose received by the patient 18 and the image quality in different portions of the image may be customized based on the circumstances.

Figure 10:
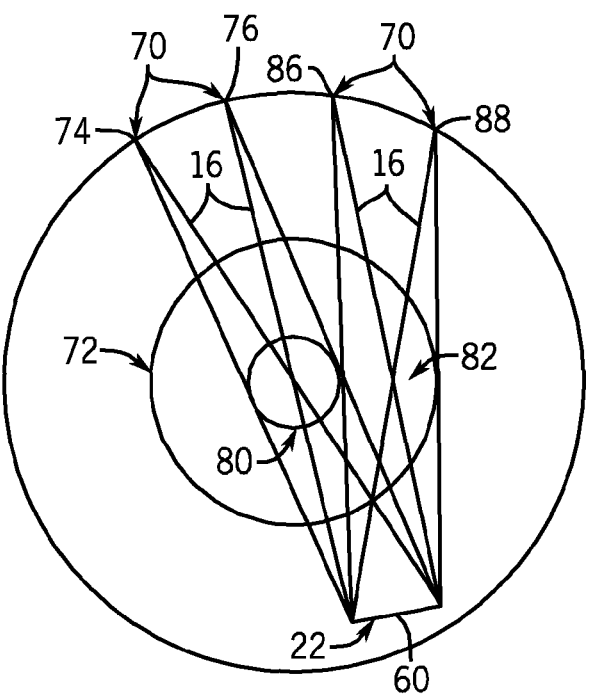
FIG. 10 is an in-plane view of four X-ray emission points in an arbitrary field-of-view configuration, in accordance with a present embodiment.

Likewise, the use of additional emission points 70 may be extended to arbitrary configurations or to configurations with a distinct central region of interest 80, such as a cardiac field of view 80, as discussed with regard to FIG. 7. For example, referring to FIG. 10, the first and second emission points 74, 76 may circumscribe the central region of interest 80 of the field of view 72. Conversely, the third and fourth emission points 86, 88 may circumscribe the peripheral region 82 of the field of view 72. The emission points 70 may be differentially operated or constituted, as discussed with regard to FIGS. 7 and 9, such that patient dosage may be adapted or adjusted based on circumstance. For example, the third and/or fourth emission points 86, 88 may not be activated or may be activated for only a subset of the possible view angles when the peripheral region 82 is of less or no interest. Similarly, if the peripheral region 82 is of less interest, the third and fourth emission points 86, 88 may be activated at lower quality, such as using a low flux or a large focal spot size.

As with the preceding examples, because the entire field of view 72 is not covered by a single emission point 70 and detector 22, the in-plane size of the detector 22, such as flat-panel detector 60, may be smaller than if a single emission point 70 were employed. Similarly, half-scan data acquisition using the first and second emission points 74, 76 may be used to acquire data for reconstructing the central region of interest 80, i.e., 180°+some additional angle of rotation. However, a full rotation, i.e., 360°, of the first, second, third, and fourth emission points 74, 76, 86, 88 may be needed to acquire data for reconstructing the full field of view 72, i.e., to fully reconstruct the peripheral region 82.

While the preceding examples depict configurations employing two or four emission points 70 to simplify illustration of the present concepts, the disclosed techniques extend to other configurations in which more than one emission point 70 is present. Similarly, field of view configurations other than those depicted are not excluded from the present technique and may benefit from the use of multiple emission points 70, as discussed herein.

Figure 11:
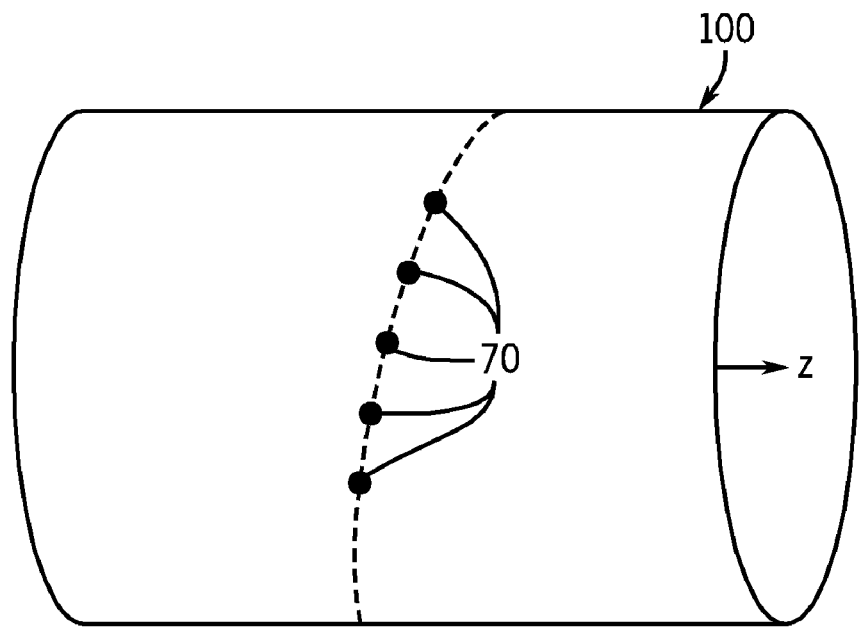
FIG. 11 is a perspective view of a CT scanner having a configuration of emission points that are offset along the longitudinal axis, in accordance with a present embodiment.

Furthermore, keeping in mind the distributed X-ray source configurations of FIGS. 3 and 4, it may sometimes be desirable to offset the emission points 70 in the z-direction. For example, as shown in FIG. 11, a z-offset may be applied to consecutive emission points 70, resulting in a slightly tilted array, relative to the primary axes of the CT scanner 100, of emission points 70. This may be particularly useful for helical cone-beam acquisitions, because the resulting dataset may be reordered to emulate an acquisition obtained with a single emission point. To achieve such a result, the z-offsets, and therefore the pitch of the resulting array, will depend on the helical pitch employed during image acquisition. The z-offsets may be adjusted to accommodate a desired helical pitch.

Figure 12:
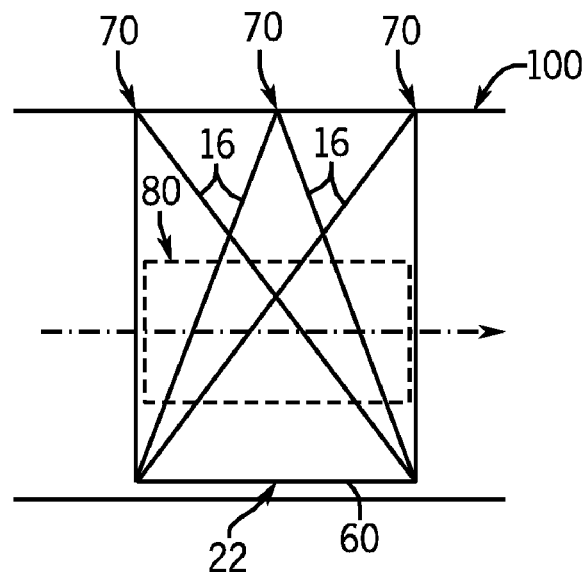
FIG. 12 is a side view of multiple axial X-ray emission points and a detector, in accordance with a present embodiment.

In addition, for cone-beam and volumetric CT geometries, it may be desirable to include additional emission points 70 along the longitudinal axis. In particular, the use of multiple emission points 70 along the longitudinal axis may allow the axial extent of the detector 22 to be reduced instead of or in addition to the reduction of the in-plane extent of the detector discussed above. For example, referring to FIG. 12, three emission points 70 deployed along the longitudinal axis of a CT scanner 100 are depicted. The emission points 70 may be fired alternatingly, such as sequentially, so that only one emission point 70 is active at a time. A detector 22, such as flat-panel detector 60, with a reduced axial extent may be employed in conjunction with the multiple longitudinal emission points in a manner analogous to that discussed in the preceding examples. As in the preceding examples, implementations of the present technique longitudinally allow for the use of smaller cone angles and therefore smaller detectors 22 longitudinally.

Figure 13:
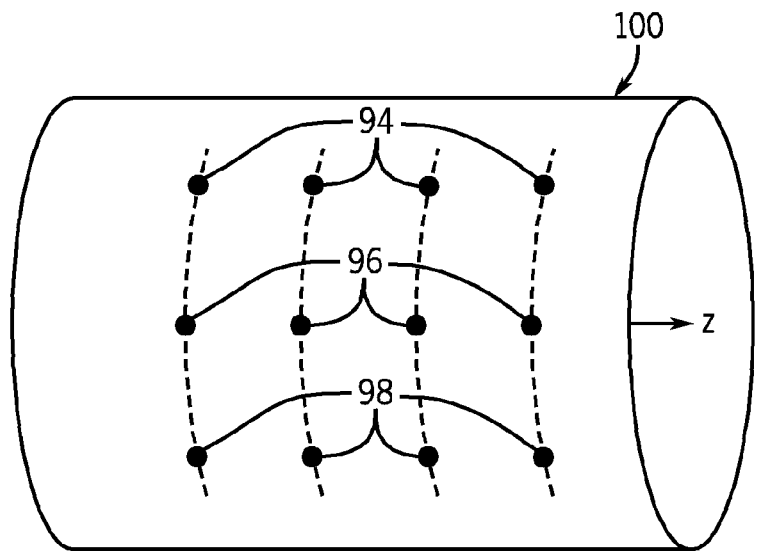
FIG. 13 is a perspective view of a CT scanner having a duplicate configuration of emission points along the longitudinal axis, in accordance with a present embodiment.

For example, referring to FIG. 13, three sets of duplicate emission points 94, 96, 98 are depicted along the longitudinal axis of a CT scanner 100. In the depicted example, each set of duplicate emission points 94, 96, 98 share coordinates within the xy-plane, but differ in their position on the z-axis, i.e., longitudinally.

As described in the preceding in-plane offset and longitudinal offset examples, the techniques disclosed herein may provide a variety of benefits. For example, the reduced in-plane and/or longitudinal extent of the detector 22 may allow smaller, less expensive detectors, such as flat-panel detectors 60, to be employed (FIGS. 5-10 and 12). In general, it is easier and less expensive to manufacture a smaller detector, particularly a flat-panel detector.

In addition, the present techniques may provide greater spatial resolution, particularly away from the isocenter. In particular, a single emission point may be associated with a large fan angle and a correspondingly large detector. The focal spot associated with the emission point looks bigger at the edge of the detector due to an increase in the so-called apparent focal-spot size. The increased apparent focal-spot size may lead to inferior spatial resolution at the edges of the detector compared to the center of the detector. The reduced fan angles and smaller in-plane extent of detectors 22 used in conjunction with the present technique (FIGS. 5-10 and 12) may allow spatial resolution to be improved away from the isocenter, i.e., over the rest of the field of view, due to the smaller apparent focal size of the emission points 70.

Furthermore, the use of multiple emission points 70 (FIGS. 5-10) may allow for dynamic flux control during an image acquisition. For example, the multiple emission points 70 may be differentially activated based on view angle to maintain uniformity of the signal at the detector 22 and, thereby, improve efficiency and limit the dynamic range at the detector, or in order to optimize the dose or image quality. In particular, in medical imaging contexts, the patient 18 (FIG. 1) typically is elliptical in cross-section, resulting varying path lengths through the patient 18, i.e., the path length an X-ray traverses through the patient 18 varies depending on the view angle position relative to the patient 18. Conventional CT techniques may employ a bowtie filter, adapted to the general cross-section of the body region being imaged, to compensate for these varying path lengths.

The present techniques, however, allow for the real time flux modulation based on the anatomy of the patient 18, i.e., a virtual dynamic bowtie. In particular, at view angles corresponding to a short path length through the patient 18, such as through the chest and back, an emission point 70 may be activated to emit X-rays having lower flux. Conversely, at view angles corresponding to a long path length, such as from shoulder to shoulder, an emission point 70 may be activated to emit X-rays having higher flux. Similarly, for intermediate path lengths, the flux of the emitted X-rays may be suitably adjusted. Furthermore, the flux associated with a view angle position may be dynamically adjusted as a patient is linearly displaced through the CT scanner. In this manner, the effects of a bowtie filter may be replicated while allowing dynamic adjustment to maintain uniformity of signal at the detector 22. Furthermore the flux for respective X-ray focal spots and views may be adjusted to minimize radiation dose to sensitive organs and to optimize the image noise in a region of interest.

The present techniques may also allow for the use of various detector technologies, such as energy discrimination detectors, so that CT techniques such as energy discrimination CT may be performed. Because of the smaller detector extent in the in-plane and/or longitudinal directions, such exotic technologies may more affordably be implemented. Similarly, such detectors may also be more easily manufactured to accommodate the reduced detector dimensions associated with the present techniques. In addition, the smaller fan angles and cone angles associated with the present technique reduce scatter in the X-ray intensity measurements and may allow the anti-scatter grid to be omitted from the detector, thereby increasing detector efficiency.

The preceding discussion relates various physical configurations of source emission points 70 in x and z dimensions and detectors 22 suitable for use in imaging systems. In certain embodiments, the emission points 70 and/or detector(s) 22 may be operated in accordance with one or more sequences of commands or instructions that define certain operational parameters of each emission point, i.e., focal spot, and/or detector separately. For example, a command sequence may define the order in which focal spots are activated, i.e., fired, the duration for which each focal spot is fired, the energy at which each emission point 70 is fired, the mA associated with a focal spot activation, the duration of a focal spot activation, and so forth. Thus, a given command sequence may define a focal spot firing pattern in which no focal spots are concurrently fired, some focal spots are concurrently fired, some focal spots are fired more or less often than others, and/or a sequential or non-sequential firing order for focal spots. In this manner, a command sequence may be selected that achieves certain goals, such as minimizing cardiac over-scan, minimizing helical over-scan, improving image quality, reducing noise, reducing scatter, reducing X-ray source thermals, limiting patient dose, and so forth. For a given patient, the appropriate command sequence may, in certain embodiments, be computed based on an initial scout scan, such as a scan acquired using a conventional command sequence using a standard bowtie filter. As will be appreciated, the instructions for the various command sequences discussed herein may be stored in and accessed from a suitable sequence buffer 32, as discussed with respect to FIG. 1. Alternatively, the command sequence could be computed ad hoc or "on-the-fly", for example using a closed loop feedback based on the detector measurements.

Figure 14:
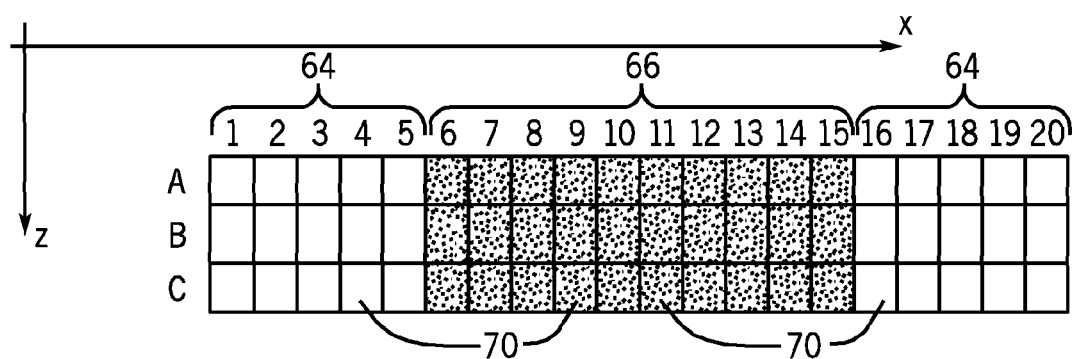
FIG. 14 depicts an array of focal spots of a distributed X-ray source in accordance with a present embodiment.

With regard to the following discussion of command sequences, and referring now to FIG. 14, focal spot series in z are labeled alphabetically, i.e., A, B, C, while the focal spot series in x are numbered, i.e., 1 to 20. In the depicted example, and as discussed in greater detail below, outer focal spots 64 may correspond to an outer radial field of view in certain embodiments. Likewise, inner focal spots 66 may correspond to an inner circular field of view, such as a cardiac field of view, in certain embodiments.

With the foregoing naming conventions in mind, a standard sequential activation sequence for a distributed source having discrete focal points in x and z is described. In this example, the distributed X-ray source is a 3×20 array of focal points as depicted in FIG. 13. Such a distributed X-ray source may be sequentially activated via a command sequence stored in a sequence buffer, such as sequence buffer 32 of FIG. 1. Such a sequential command sequence may correspond to an activation order such as: A1-A2-A3- . . . -A20-B1-B2-B3- . . . -B20-C1-C2-C3- . . . -C20-A1-A2-A3- . . . -A20- . . . and so forth. Alternatively, another example of a sequential command sequence might be A1-B1-C1-A2-B2-C2-A3- . . . -A20-B20-C20-A1-B1-C1-A2- . . . and so forth. Thus, in these examples, emission point activation may proceed sequentially by row or column. In other examples, alternative patterns may be employed, such as spiral patterns, zig-zag patterns, Pseudo-random patterns, and so forth. In these sequential examples there is a fixed or pre-determined order and the activation proceeds sequentially based on that fixed pre-determined order.

In other embodiments, the command sequence may be non-uniform. In some such embodiments, certain focal spots may be fired, i.e., activated, more frequently than other focal spots. For example, focal spots that fire through highly attenuating portion of a patient or object and/or that fire through regions of interest of interest that require good image quality may be fired more frequently (instead of or in addition to being fired with higher mA, kW, and/or dwell time). Conversely, focal spots that fire through low attenuating portions of the patient or object and/or that fire through sensitive organs may be fired less frequently (instead of or in addition to being fired with lower mA, kW, and/or dwell time). One example of such a non-uniform command sequence might include sequentially activating all of the focal spots (A1→C20) of a distributed X-ray source followed by sequentially activating only the inner focal spots 66 (A6→A15, B6→B15, C6→C15) and repeating these respective command sequences. Thus, in this example, the inner focal spots 66 are activated twice as often as the outer focal spots 64. In another example, some focal spots may not be activated at all. For example, in implementations where only a small portion of the patient or object is of interest, only the inner focal spots 66 may be activated (A6→A15, B6→B15, C6→C15). As will be appreciated, other combinations of firing (or not firing) focal spots may also be employed such that different focal spots or subsets of focal spots are activated more or less often than other focal spots or subsets of focal spots.

In another embodiment, two or more focal spots may be activated simultaneously. Such an embodiment may be useful where the simultaneously activated focal spots generate X-rays incident on different portions of the detector 22 or on different detectors 22. For example, focal spots associated with rows A and C may be collimated in z such that each row of focal spots fires on a different longitudinal portion of the detector 22 so that there is little or no overlap on the detector 22 if focal spots on rows A and C are simultaneously activated. In this example, focal spots in rows A and C can be activated simultaneously, such as in accordance with the command sequence: A1C1-B1-A2C2-B2-A3C3-B3- . . . -A20C20-B20-A1C1-B1- . . . .

In implementations employing more than one detector 22, such as depicted in FIG. 4, focal spots may be collimated such that they are detected by only one of the available detectors 22. In such an implementation, focal spots collimated to illuminate one detector 22 may be activated simultaneously with focal spots collimated to illuminate a different detector 22. By employing two or more smaller detectors in this manner, the greater flux of a single, larger area detector may be achieved while allowing the greater resultant scatter to be managed and mitigated in a way that adapts to the anatomy or object being scanned.

In such embodiments where simultaneous activation of focal spots is employed, the additional cross-scatter may be generated. Thus, a decision as to whether simultaneous activation of focal spots may be made based on the object undergoing imaging, the expected path lengths through the object for each focal spot (since greater path lengths generally correspond to greater scatter potential), the position of each focal spot (to optionally avoid simultaneously activating focal spots whose X-rays are incident on a detector or detectors too closely together), the expected detectable signal for each focal spot (to optionally avoid simultaneously activating focal spots that have a large difference in the expected detectable signal). In certain embodiments, focal spots can be selected for simultaneous activation where the expected path lengths are substantially equivalent. In the event of substantial differences in the path length, the focal spots having the lower path length (and, therefore, the lower attenuation) may be activated with a lower mA to equalize the received primary flux and to reduce the cross-scatter into the detector having the receiving the lower signal.

Furthermore, in certain embodiments, during a given "sample period" or activation interval, one focal spot may be activated for some portion of the period and another focal spot activated for a different period that may or may not overlap in time with the first time period, i.e., focal spots may have complementary dwell times. To the extent that net cross-scatter is present, this may be directly measured by occasionally turning on a source by itself rather than simultaneous with another.

In addition, in certain embodiments a command sequence can be constructed that mitigates motion artifacts. For example, for a coronary vessel moving mostly in the xy plane along the y-axis, a focal point aligned with the direction of motion will see the least motion. Thus, a command sequence which emphasizes activation of focal points aligned with structures in motion, either by increasing frequency of activation or dwell time, may be used to minimize motion artifacts in the reconstructed images.

Further, in certain embodiments, focal spots of different sizes or scales may be employed, with different sizes of focal spots being more suitable for imaging different sizes of structures. For example, in a cardiac implementation, a command sequence may be employed that emphasizes activation of small focal spots that cover small structures in the region of interest, such as the coronary vessels.

Generally there is flexibility in terms of the sequence in which individual focal spots may be activated, in terms of whether focal spots are simultaneously activated, in terms of absolute mA associated with individual focal spots, in terms of relative mA associated with simultaneously activated focal spots, and in terms of complementary dwell times provided for each focal spot. Instead, these various factors may be varied at the individual focal spot level or with respect to some or all of the focal spots provided that there is no confusion possible at the detector or readout level as to which focal spot the detected X-rays originated from, i.e., as long as there is no overlap at the detector(s). Indeed, in certain embodiments, an exhaustive evaluation of possible sub-sequences or sequences may be performed, with the command sequence being selected that provides the desired trade-off between sampling, dose-efficiency, scatter, image noise, temporal resolution, and spatial resolution.

In addition to non-uniform command sequences of focal points, other command sequences may be employed that are suitable for addressing cardiac half-scan over-scan issues. In conventional third-generation CT systems, a "half-scan" consists of 180°+α rotation interval where α is the fanangle, which can be the physical fanangle of the X-ray beam or the fanangle corresponding to a field of view of interest. A dataset obtained in a half-scan of rotation is typically rebinned to correspond to a parallel-beam acquired set or is reconstructed as is using a Parker-weighting scheme. The extra rotation over the fanangle results in additional dose to the patient or object being scanned compared to parallel beam acquisitions. For example, referring to FIG. 15, a prior art view depicting the useful projection data 80 and the wasted dose 82 acquired using a half-scan acquisition scheme is depicted in r-theta coordinates where r is the distance of a ray relative to isocenter and theta is the angle of a ray relative to a vertical axis.

Figure 15:
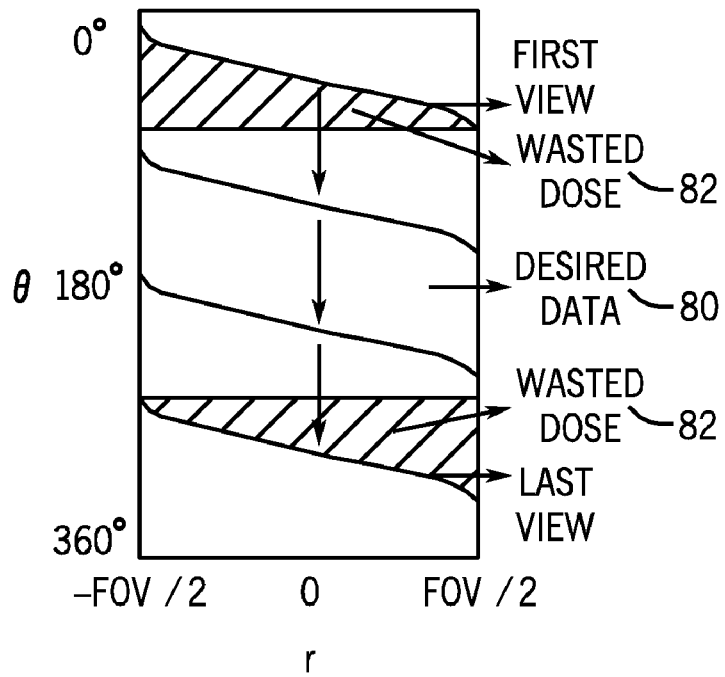
FIG. 15 depicts a prior art r-theta diagram of a half-scan over-scan acquisition scheme.
Figure 16:
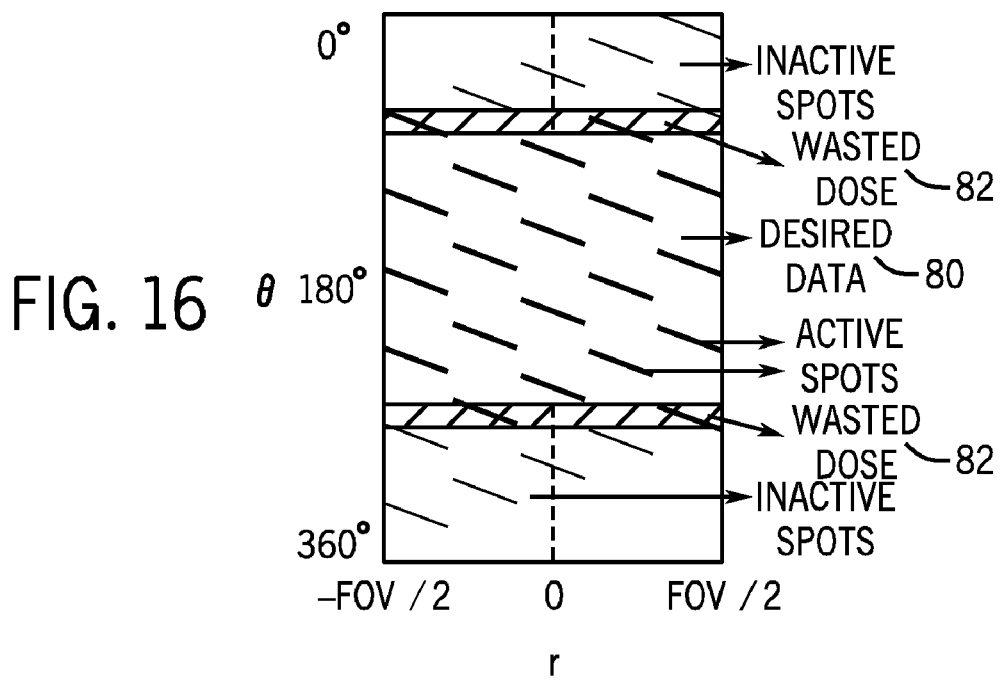
FIG. 16 depicts an r-theta diagram of a half-scan over-scan acquisition scheme performed in accordance with a present embodiment.

Using a distributed X-ray source and a suitable activation scheme, as discussed herein, the wasted dose associated with half-scan acquisitions may be reduced. For example, in one embodiment, the range of active focal spots, i.e., emission points, can gradually be extended as the focal spots rotate in the 180° parallel beam range (or 90° in a two detector implementation, 60° in a three detector implementation, and so forth). As the X-ray source rotates out of the parallel beam range of interest, the focal spots may be gradually deactivated. Turning now to FIG. 16, a r-theta coordinate diagram is depicted illustrating the useful data and wasted dose associated with this technique. As seen in FIGS. 15 and 16, the wasted does associated with the technique of this example is reduced relative to conventional half scan acquisition techniques.

Similarly, in helical scan modes, some X-ray dose may be wasted at the edge of the helix. A distributed source topology may avoid such wasted does when controlled by an activation scheme that gradually activates and deactivates focal spots (along z as opposed to x) as they enter and exit the longitudinal region of interest. In this manner, the helical over-scan problem maybe addressed.

Further, the commands stored in the sequence buffer can optimize the timing of the respective X-ray pulses and detector readouts such that the corresponding measurements are well aligned in r-theta space (Radon space), for efficient data rebinning or image reconstruction.

External information, such as an ECG sequence may be taken into account in implementing a command sequence stored in the sequence buffer 32. For example, in a prospective gating acquisition, an ECG signal may be used to determine when the heart is at the desired phase for imaging. In such embodiments, there may be gantry angle dependence provided in the sequence, such as where a virtual bowtie filter is being implemented as part of the command sequence. Thus, in such embodiments, X-rays might not be generated until partway through the buffer, i.e., instructions in the sequence buffer may be conditional on gantry position and ECG trigger such that some instructions might not be implemented until the desired conditions are initially met. Similarly, a related embodiment might employ a "JUMP" or "GOTO" command in the stored sequence to proceed to execute a set of instructions once the ECG trigger and/or gantry position is determined to be suitable.

Alternatively, a similar approach may be implemented in the form of instructions to the DAS stored in the sequence buffer 32. For example, the instructions in the sequence buffer may be operated in a loop mode and may be sequenced through without executing until the desired gantry angle and/or ECG trigger occurs. At this time, i.e., when acquisition conditions are met, an "Exposure On" command may be issued and, when the next super view begins the logic stored in the sequence buffer will begin executing normally.

Thus, commands or instructions stored as a command sequence may relate to the operation of distributed X-ray sources and the control of the X-ray controller 30 or to operation of the DAS 36. For example, scheduled adjustments to data acquisition might be provided as part of the list of instructions on the sequence buffer. In one example, there might be electronic noise benefits to longer sub-views (DAS sampling interval) when the flux is low. Thus, when sequence buffer instructions to the X-ray controller 30 result in a low flux, a corresponding instruction may be placed in the sequence buffer to increase the sampling interval of the DAS 36 for the duration of the low flux. Similarly, when a dual kVp scan is being performed, commands to switch the kV could also be stored in the sequence buffer 32.

Technical effects of the invention include the use of two or more discrete emission points and one or more corresponding detectors to image a field of view. The operation of the two or more discrete emission points may be independent of one another. The operation of the respective emission points and/or readout of the detectors may be performed in accordance with commands stored in a sequence buffer.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A CT imaging system comprising:
   a solid-state or thermionic X-ray source comprising a plurality of discrete X-ray emission focal spots, wherein the solid-state or thermionic X-ray source is configured as a stationary ring or as a stationary or rotating array of the discrete X-ray emission focal spots;
   one or more detectors configured to detect X-rays emitted by the plurality of X-ray emission focal spots;
   an X-ray controller configured to independently operate the plurality of discrete X-ray emission focal spots;
   a data acquisition system configured to readout signals from the one or more detectors; and
   a sequence buffer which, when at least the X-ray controller is operated, physically encodes a list of commands controlling the operation of the X-ray controller, wherein the size of the sequence buffer is based at least in part on the length and number of commands physically encoded in the sequence buffer.

2. The CT imaging system of claim 1, wherein the sequence buffer physically encodes a second list of commands controlling the operation of the data acquisition system.

3. The CT imaging system of claim 2, wherein the second list of commands includes one or more of a command instructing the data acquisition system to adjust a sampling period, to begin data readout, or to cease data readout.

4. The CT imaging system of claim 1, wherein the solid-state or thermionic X-ray source comprises a distributed X-ray source in which the respective emission points are separated by distances of 30 cm or less.

5. The CT imaging system of claim 1, wherein the list of commands includes one or more commands instructing the X-ray controller to activate a respective X-ray emission focal spot at a specified time or in a specified sequence, at a specified mA, for a specified duration, at a specified focal spot size, at a specified interval after a trigger, at a specified energy, or at a specified kVp.

6. The CT imaging system of claim 1, wherein each command of the list of commands corresponds to the operation an X-ray emission focal spot at a respective view.

7. The CT imaging system of claim 1, wherein each X-ray emission from the plurality of discrete X-ray emission focal spots is defined by a different command of the list of commands.

8. A sequence buffer comprising:
   a data storage structure;
   a command sequence physically encoded on the data storage structure, wherein the command sequence comprises instructions for independently operating a plurality of X-ray emission focal spots of a distributed X-ray source.

9. The sequence buffer of claim 8, wherein the command sequence further comprises instructions for operating a data acquisition system for reading out data from one or more detectors.

10. The sequence buffer of claim 9, wherein the instructions for operating the data acquisition system comprise instructions for adjust a sampling period, for beginning data readout, or for ceasing data readout.

11. The sequence buffer of claim 8, wherein the instructions for independently operating the plurality of X-ray emission focal spots comprise instructions for activating a respective X-ray emission focal spot at a specified time or in a specified sequence, at a specified mA, for a specified duration, at a specified interval after a trigger, at a specified energy, at a specific focal spot size, or at a specified kVp.

12. The sequence buffer of claim 8, wherein the data storage structure comprises a solid state memory device, an optical storage medium, or a magnetic storage medium.

13. A method comprising:
processing a list of commands related to the operation of an imaging system;
individually operating a plurality of X-ray focal spots of a distributed X-ray source in accordance with the list of commands.

14. The method of claim 13, wherein individually operating the plurality of X-ray focal spots comprises activating the X-ray focal spots in a non-uniform manner with respect to one or more of sequence, mA, kVp, or duration.

15. The method of claim 13, wherein individually operating the plurality of X-ray focal spots comprises activating two or more X-ray focal spots simultaneously.

16. The method of claim 13, wherein individually operating the plurality of X-ray focal spots comprises activating and deactivating the X-ray focal spots to reduce half-scan overscan.

17. The method of claim 13, wherein individually operating the plurality of X-ray focal spots comprises activating and deactivating the X-ray focal spots to reduce helical over-scan.

18. The method of claim 13, comprising operating a data acquisition system in accordance with the list of commands.

19. The method of claim 18, wherein operating the data acquisition system comprises conditionally reading out one or more detectors.

20. The method of claim 18, wherein operating the data acquisition system comprises beginning data acquisition based on a gantry position and/or a cardiac phase signal.

21. The method of claim 13, wherein the list of commands are stored in a buffer.

22. The method of claim 13, wherein the list of commands are generated using feedback based on measured X-ray levels at a detector.

23. A method comprising:
providing a distributed X-ray source comprising a plurality of discrete and separately operable X-ray emission focal spots;
providing one or more detectors configured to generate signals in response to X-rays emitted by the distributed X-ray source;
providing a sequence buffer capable of storing a list of commands for operating the plurality of X-ray emission focal spots;
electrically connecting an X-ray controller to the distributed X-ray source and the sequence buffer, wherein the X-ray controller is capable of independently operating the plurality X-ray emission focal spots in accordance with the list of commands; and
electrically connecting a data acquisition system to the one or more detectors, wherein the data acquisition system is capable of reading out the signals generated by the one or more detectors.

24. The method of claim 23, wherein the data acquisition system is operated in accordance with the list of commands.

* * * * *

UNITED STATES PATENT AND TRADEMARK OFFICE
CERTIFICATE OF CORRECTION

| | | |
|---|---|---|
| PATENT NO. | : 7,885,375 B2 | Page 1 of 1 |
| APPLICATION NO. | : 12/254732 | |
| DATED | : February 8, 2011 | |
| INVENTOR(S) | : Bernard De Man et al. | |

It is certified that error appears in the above-identified patent and that said Letters Patent is hereby corrected as shown below:

In Column 1, Line 20, delete "R01" and insert -- 1 R01 --, therefor.

In Column 11, Line 65, delete "2300 degrees" and insert -- 230° --, therefor.

Signed and Sealed this
Twenty-sixth Day of April, 2011

David J. Kappos
*Director of the United States Patent and Trademark Office*